US 7,738,097 B2

(12) United States Patent
Khetani et al.

(10) Patent No.: US 7,738,097 B2
(45) Date of Patent: Jun. 15, 2010

(54) METHOD FOR USING A PHOTONIC CRYSTAL FIBER AS A RAMAN BIOSENSOR

(75) Inventors: Altaf Khetani, Kanata (CA); Majid Naji, Ottawa (CA); Neil Lagali, Ottawa (CA); Hanan Anis, Ottawa (CA); Rejean Munger, Ottawa (CA)

(73) Assignee: University of Ottawa, Ottawa, Ontario (CA)

( * ) Notice: Subject to any disclaimer, the term of this patent is extended or adjusted under 35 U.S.C. 154(b) by 160 days.

(21) Appl. No.: 12/174,313

(22) Filed: Jul. 16, 2008

(65) Prior Publication Data
US 2010/0014077 A1 Jan. 21, 2010

(51) Int. Cl.
*G01J 3/44* (2006.01)
*G01N 21/65* (2006.01)
*G02B 6/32* (2006.01)
(52) U.S. Cl. .................. 356/301; 385/125
(58) Field of Classification Search .............. 356/301; 385/125
See application file for complete search history.

(56) References Cited

U.S. PATENT DOCUMENTS

| 7,595,882 B1 * | 9/2009 | Chen et al. .......... 356/437 |
| 2007/0020144 A1 * | 1/2007 | Du et al. .......... 422/58 |

OTHER PUBLICATIONS

Yan et al., "Hollow core photonic crystal fiber surface-enhanced Raman probe", Applied Physics Letters, 89, 204101, Nov. 15, 2006.*
Zhang et al., "Liquid core photonic crystal fiber sensor based on surface enhanced Raman scattering", Applied Physics Letters, 90, 193504, May 8, 2007.*
Danny Noordegraaf, et al., "Electrically and mechanically induced long period gratings in liquid crystal photonic bandgap fibers." Optics Express Jun. 25, 2007/ vol. 15, No. 13.
F.M.Cox et al., "Liquid-filled hollow core microstructured polymer optical fiber." Optics Express May 1, 2006/vol. 14, No. 9.
T. A. Birks, et al., "Scaling laws and vector effects in bandgap-guiding fibres." Optics Express Jan. 12, 2004/vol. 12, No. 1.
Sylvie Lebrun et al., "High-efficiency signle-mode Raman generation in a liquid-filled photoic bandgap fiber." 2007 Optical Society of America.
G. Antonopoulos, et al. "Experimental demonstration of the frequency shift of bandgaps in photonic crystal fibers due to refractive index scaling." Optics Express Apr. 3, 2006/vol. 14, No. 7.

* cited by examiner

*Primary Examiner*—F. L Evans
(74) *Attorney, Agent, or Firm*—Harness, Dickey & Pierce PLC

(57) ABSTRACT

A method is provided for biosensing using a photonic crystal fiber having a hollow core. The method includes: designating an analyte of interest; determining a wavelength for an excitation light source which generates a Raman spectrum when incident upon the analyte of interest; selecting a photonic crystal fiber that would guide the light when the fiber is non-selectively filled with a solvent hosting the analyte of interest; non-selectively filling a photonic crystal fiber with the solvent hosting the analyte of interest; interrogating the analyte of interest by coupling light from the light source to the photonic crystal fiber; and analyzing the light output from the photonic crystal fiber for Raman fingerprints.

16 Claims, 6 Drawing Sheets

METHOD FOR USING A PHOTONIC CRYSTAL FIBER AS A RAMAN BIOSENSOR

FIELD

The present disclosure relates to a system and method for using a photonic crystal fiber as a Raman spectroscopy platform suitable for biosensing applications.

BACKGROUND

Optical techniques have played an important role in instrumentation and sensor applications especially in non-contact measurements. It is well established that the detection and identification of bacteria, protein and pathogens as infectious agents in people, environment and food sample is very important and has been the prime focus of interest. In recent years, the advancement in optical technologies has surged in the field of sensors. Most optical based sensors are spectroscopic techniques involving fluorescence or absorbance. Although these techniques are very popular and effective they require, for instance in fluorescence, labeling of the molecule which can lead to alterations in target-receptor interactions caused by conformational changes. This has led to considerable effort investigating other alternatives.

Raman spectroscopy is a compelling technique. It provides an optical fingerprint of chemicals and biomolecules corresponding to the vibrational frequencies of molecular bonds. Therefore, this label-free optical sensing technique has the ability to quantify molecules attached to the sensing surface, which should improve the well known problem of non-specific binding in all solid surface sensing systems. Additionally, it is desirable to have a small, rapid assays that use small sample volumes and capable of detecting several compounds of species in parallel. This is significant because in many cases, sample collection is limited and sample processing also requires time. All of these factors point toward being able to detect multiple agents in parallel using small sample volumes.

One of the principle drawbacks of Raman spectroscopy is a weak Raman signal. Signal strength may be improved by increasing laser intensity, enhancing the quality of transverse beam profile or increasing the laser beam interaction length in the analyte media. A hollow-core waveguide that supports a single transverse mode with low attenuation losses and long interaction length might meet the requirements for enhancing a Raman signal. This disclosure is the first to contemplate non-selectively filling a hollow-core photonic crystal fiber for biosensing applications. Photonic crystal fiber offers a medium with long interaction lengths which enhance the Raman signal, thereby enabling the use of low-cost, low-power lasers and detectors. Thus, non-selectively filled photonic crystal fibers can provide an improved platform for performing Raman spectroscopy.

The statements in this section merely provide background information related to the present disclosure and may not constitute prior art.

SUMMARY

A method is provided for biosensing using a photonic crystal fiber having a hollow core. The method includes: designating an analyte of interest; determining a wavelength for an excitation light source which generates a Raman spectrum when incident upon the analyte of interest; selecting a photonic crystal fiber that would guide the light when the fiber is non-selectively filled with a solvent hosting the analyte of interest; non-selectively filling a photonic crystal fiber with the solvent; interrogating the analyte of interest by coupling light from the light source to the photonic crystal fiber; and analyzing the light output from the photonic crystal fiber for a Raman effect.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Raman spectroscopy is based on a light scattering phenomenon known as "Raman effect". When a monochromatic light is incident on an atom or molecule, a fraction of light is scattered and other is absorbed. Most of the scattered light is elastically scattered known as Rayleigh scattering, which has same wavelength and frequency as the incident light. However, a small fraction (1 in 1 million) of photons is scattered at different frequency, usually lower than the incident light. The amount of energy corresponding to shift in wavelength is due to the vibrational and rotational energy level of the molecules of the sample. The spectrum caused due to shift in frequency is known as Raman Spectrum and the phenomenon is called the Raman effect. Raman spectra usually contain many sharp peaks corresponding to the specific molecular vibrational frequencies and thus give a clear signature of the presence of specific molecules in the sample. Raman spectra can therefore be used to discriminate between several chemical species in materials for qualitative and quantitative analysis.

Photonic crystal fibers have unique properties which appear to provide a promising platform for Raman spectroscopy. A hollow-core photonic crystal fiber (HC-PCF) is comprised of an air core surrounded by a cladding consisting of a periodic array of air holes. The periodic cladding structure prevents light in a range of wavelengths from propagating. As a result, the hollow core guides and confines the range of wavelengths. Various types of hollow-core photonic crystal fibers are readily known in the art.

Figure 1:
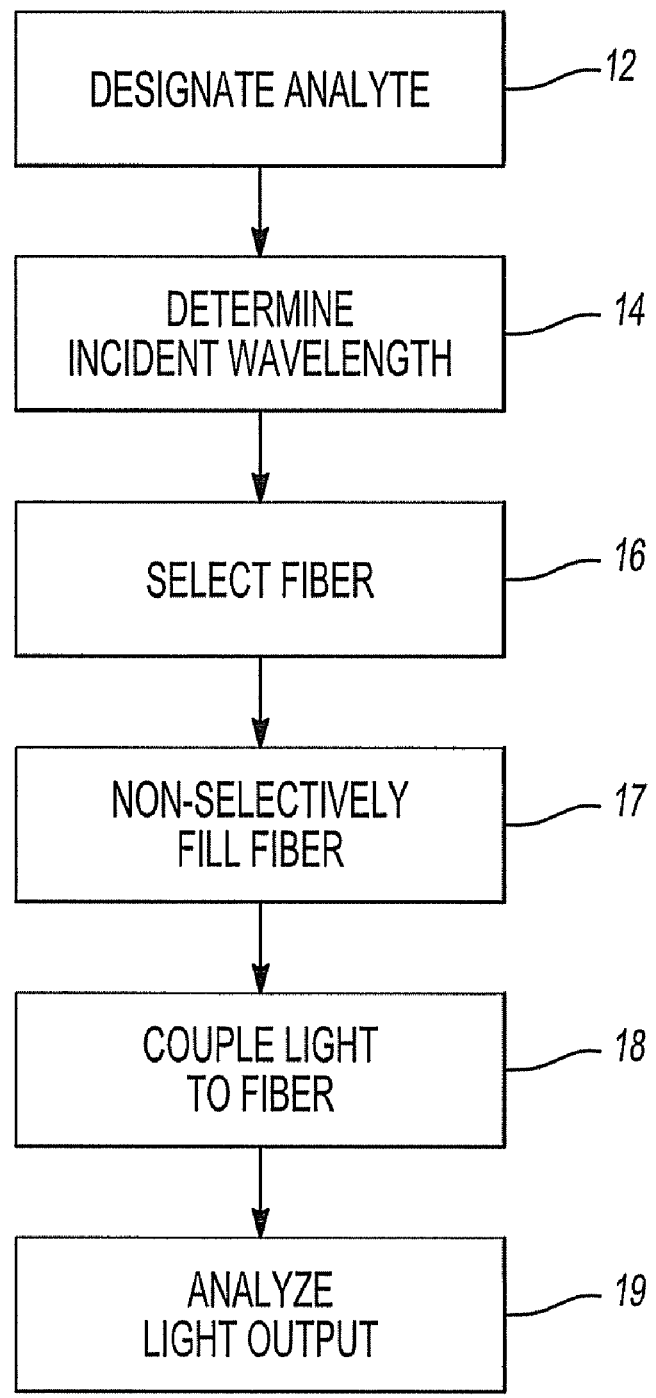
FIG. 1 is a flowchart illustrating a method for using a photonic crystal fiber as a Raman spectroscopy platform.

FIG. 1 illustrates a technique for using a hollow-core photonic crystal fiber as a Raman spectroscopy platform suitable for biosensing applications. To use as a sensor, the fiber will be filled with a sample to be analyzed. However, the guiding property of the fiber changes depending on the refractive index of the sample. Therefore, it is first necessary to determine the analyte of interest at 12, including the solvent or host for analyzing the analyte.

In an exemplary experiment, zinc oxide nanoparticles are the analyte of interest and ethanol is used as a solvent for analyzing the particles. The host of the analyte of interest is referred to herein as the sample being analyzed. Given an analyte of interest, a preferred wavelength for incident light which creates a Raman effect may be readily determined at 14 for the analyte. For zinc oxide nanoparticles, incident light having a 765 nm wavelength is preferred. While the description below makes reference to this particular experiment, it is readily understood that other types of analytes and solvent materials are within the scope of the present disclosure.

Depending upon the excitation wavelength, a fiber can be selected at 16 that would guide this wavelength when the fiber is filled with the sample. Since the bandgap of a sample filled photonic crystal fiber will shift, the fiber selection must account for this bandgap shift. The shift in bandgap can be determined using the refractive scaling laws. More specifically, the shifted wavelength is given by:

$$\lambda' = \lambda_0 \left[ \frac{1 - \left(\frac{\eta_{liq}}{\eta_{sil}}\right)^2}{1 - \left(\frac{\eta_{air}}{\eta_{sil}}\right)^2} \right]^{1/2}$$

where $\lambda_o$ is the central wavelength of the bandgap of an empty photonic crystal fiber, $\lambda'$ is the central wavelength of the shifted bandgap of the sample filled fiber; $\eta_{liq}$ is the refractive index for the liquid sample, $\eta_{air}$ is the refractive index for air and $\eta_{sil}$ is the refractive index for silica. Knowing the sample used to fill the fiber (and thus a refractive index for the same), the bandgap shift for a sample filled fiber may be computed in accordance with the refractive scaling law. Further information regarding the refractive scaling law applied herein may be found in an article by Birks et. al. entitled "Scaling laws and vector effects in bandgap-guiding fibres", Opt. Express, 12, 69-74 (2004).

To guide light having a 765 wavelength through an ethanol filled photonic crystal fiber, a hollow core photonic crystal fiber (i.e., HC-1550) with 1550 nm original central bandgap must be selected. For illustration purposes, a table of exemplary types of fibers is provided below.

Entries in the table provide shifted central wavelength and the wavelength range (in parenthesis) supported by the photonic crystal fiber when empty or filled with various solvents. It is readily understood that other types of fibers may be selected.

The selected fiber may then be filled at 17 with a sample to be analyzed. More specifically, the fiber is non-selectively filled. In other words, both the hollow core and all of the cladding holes (or channels) are filled with the sample to be analyzed. The problem of evaporation may be addressed by inserting a reservoir filled with the sample at one end of the fiber. The reservoir may use a syringe needle whose broader end is filled with the sample and glued with a glass cover slip, while the fiber is inserted at the other end. The reservoir ensures that the liquid is continuously supplied inside the fiber to replenish any evaporated liquid. Alternatively, evaporation may be circumvented by confining the sample within the fiber through pressure or by sealing the fiber ends.

Raman spectroscopy may now be carried out by coupling excitation light of the excitation light source to the photonic crystal fiber as indicated at 18. By analyzing Raman spectrum of the light output from the photonic crystal fiber at 19, the presence of an analyte of interest may be determined. In particular, we are interested in a spectrum of spontaneously scattered Raman-shift light. Different techniques for analyzing the light output are readily known in the art and may be applied to interrogate the sample contained in the fiber.

A basic construct for a biosensor suitable for implementing this technique is set forth below. The biosensor includes a coherent excitation light source, a photonic crystal fiber having a hollow core, and a light detector. The excitation light source is optically coupled to an inlet of the photonic crystal fiber and the light detector is optically coupled to an outlet of the photonic crystal fiber. The fiber is non-selectively filled with a sample to be analyzed. In operation, light from the light source is projected through the fiber. The light detector detects a Raman shift experienced by the light received from the filled photonic crystal fiber. It is to be understood that only the required components are discussed above, but that other optical components may be used to implement the biosensor.

Figure 2:
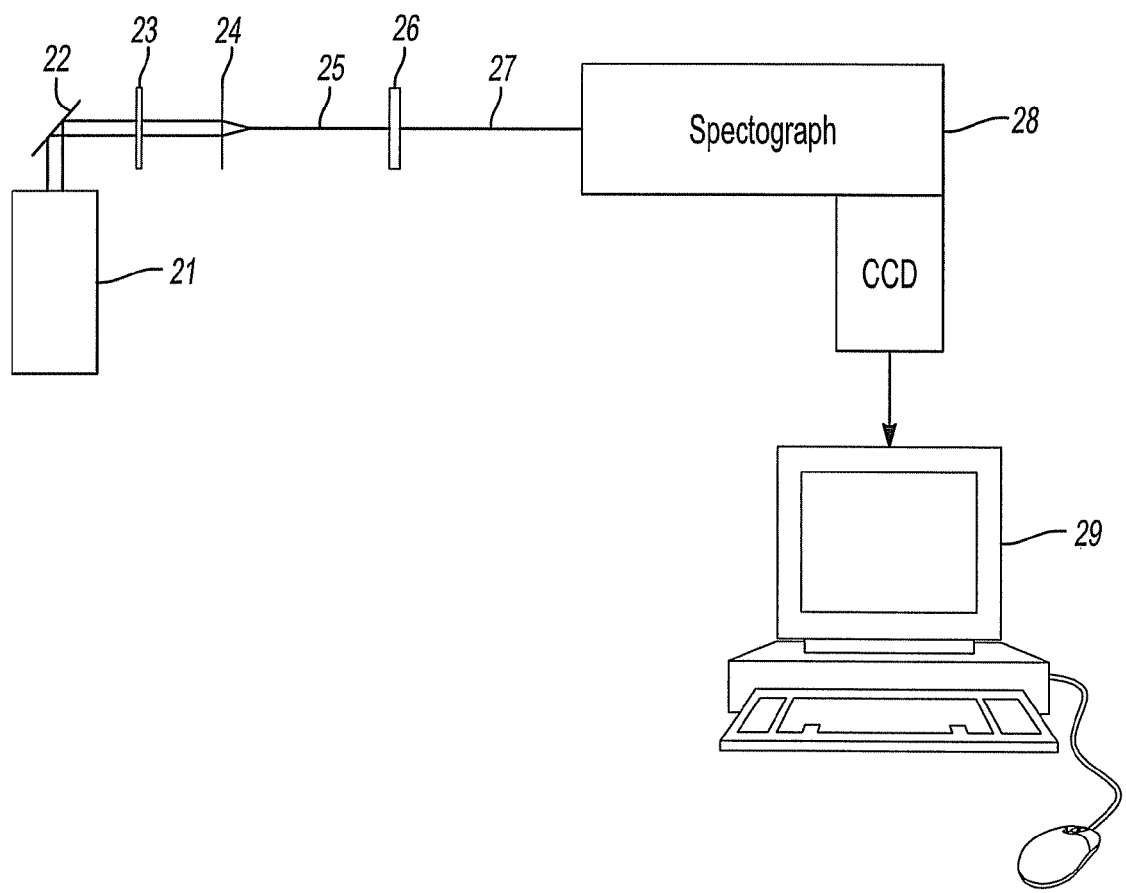
FIG. 2 is a diagram depicting an exemplary embodiment for a biosensor in accordance with the present disclosure.

FIG. 2 depicts an exemplary embodiment for a biosensor 20 in accordance with the present disclosure. In the exemplary embodiment, the excitation light source 21 projects monochromatic light having a 785 nm wavelength. The light source 21 may be implemented with a single mode 100 mW, 14 pin butterfly laser commercially available from Innovative Photonic Solutions. The laser beam from the light source 21 is directed through a silver coated mirror 22 and then passed through a band pass filter 23 (e.g., a 785 nm band pass filter commercially available from Iridian). Light passing through the filter 23 is coupled to a photonic crystal fiber 25 using an objective lens 24 (e.g., a 40× Newport microscope objective lens with NA.=0.65). Coupling laser light to a filled fiber was sensitive and spurious coupling effects had to be avoided as they caused a tremendous reduction in Raman generated signal. Accordingly, the near field laser beam pattern out of the fiber was checked to ensure that the output beam came from the core and not the fiber cladding. Other optical arrangements for coupling the light to the fiber are contemplated by this disclosure.

A fiber which would guide light having a 785 nm wavelength when filled with ethanol was selected in the manner described above. Simulation was done using a commercial software COMSOL Multiphysics version 3.1 to check guidance at 785 nm as well as to see whether the Raman shift at 890 nm is supported. This result predicts the guidance of

| Liquid | Refractive Index | Fiber Type | | | | | |
|---|---|---|---|---|---|---|---|
| | | HC-440 | HC-580 | HC-633 | HC-800 | HC-1060 | HC-1550 |
| Empty | n = 1 | 440 (410-470) nm | 580 (515-595) nm | 633 (570-690) nm | –800 (795-880) nm | 1060 (990-1150) nm | 1550 (1450-1650) nm |
| Water | n = 1.33 | 249 (232-266) nm | 328 (291-336) nm | 358 (322-390) nm | 452 (450-498) nm | 600 (560-651) nm | 877 (820-934) nm |
| Acetonitryl | n = 1.34 | 236 (220-252) nm | 311 (276-319) nm | 339 (306-370) nm | 429 (426-472) nm | 569 (531-617) nm | 832 (778-886) nm |
| Ethanol | n = 1.36 | 212 (198-227) nm | 280 (248-287) nm | 305 (275-333) nm | 386 (384-425) nm | 512 (478-555) nm | 748 (700-797) nm |

Figure 3A:
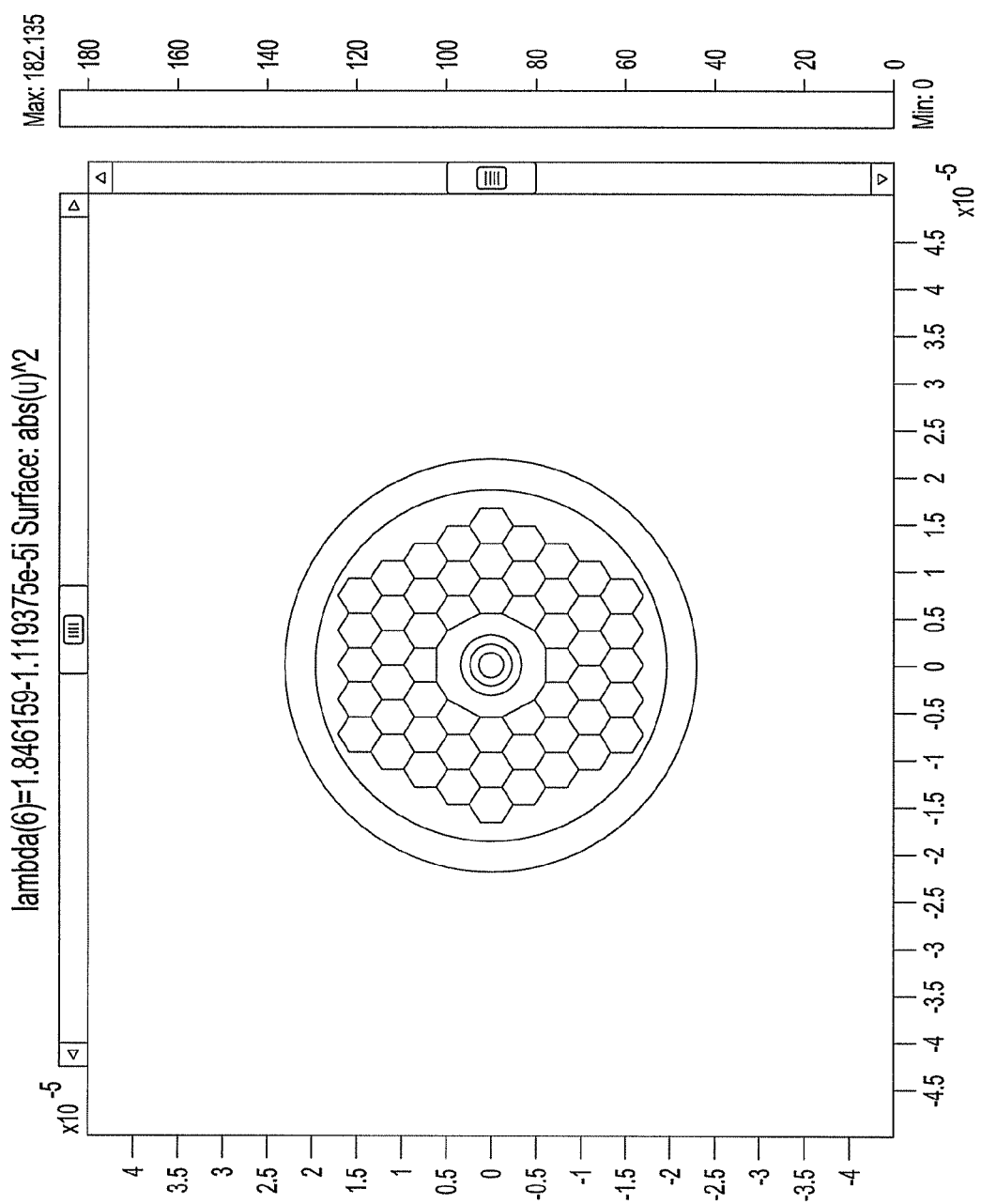
FIGS. 3A and 3B illustrate the simulated mode field intensity of light in a photonic crystal fiber at 785 nm and 890 nm, respectively.
Figure 3B:
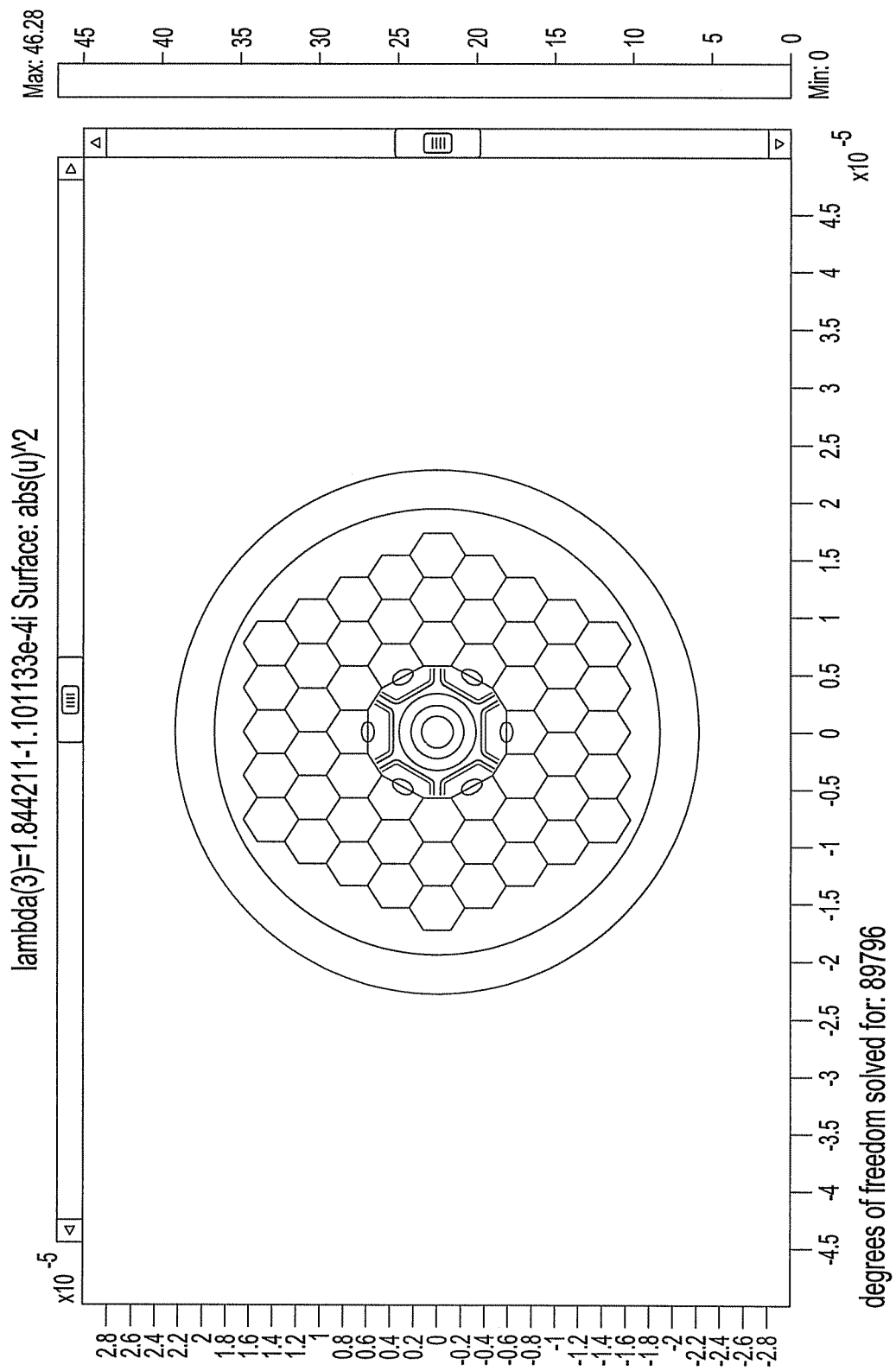

Raman-shifted light in a range up to 1500 cm$^{-1}$, which is sufficient for spontaneous Raman spectroscopic fingerprinting of a wide range of materials which can be seen from FIGS. 3A and 3B.

Light at the output of the fiber 25 was passed through a long-pass filter 26, to reduce the excitation light and then directly coupled to a collecting fiber bundle 27 consisting of 30-100 µm multimode fibers arranged in a circular pattern at the collection end and stacked in a linear fashion at the output end. Such fiber bundle is commercially available from Fiber Optic Systems Inc. The multimode fiber bundle 27 is in turn coupled into a spectrograph 28 (e.g., Kaiser f/18 spectrograph, which had a TE-cooled Andor CCD camera). The spectrometer is equipped with a noth or edge filter to reject the elastically scattered photons (Rayleigh photons) which have the same energy as the laser photons. Data processing may be performed with a computer 29 in data communication with the CCD of the spectrograph 28.

Figure 4:
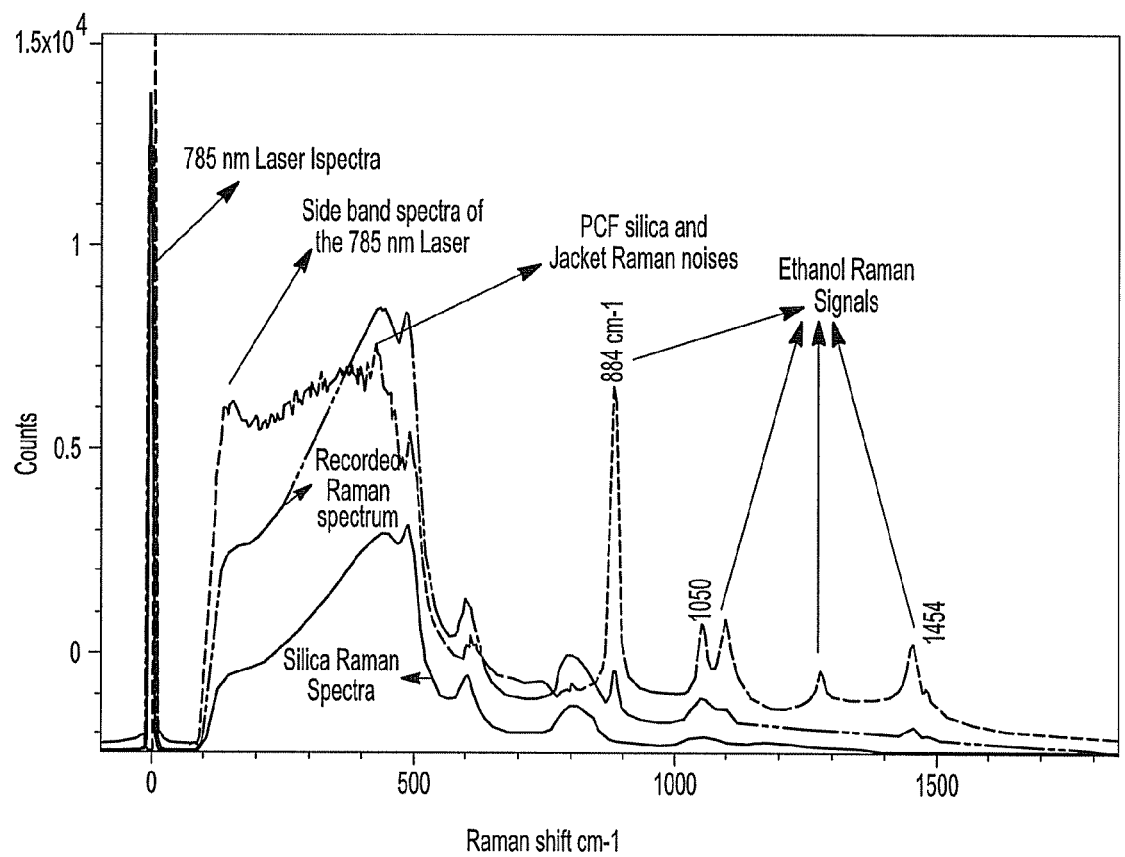
FIG. 4 illustrates the Raman spectra for pure ethanol determined by subtracting the Raman spectra of the collecting fiber bundle from the measured Raman spectrum of an ethanol-filled photonic crystal fiber.

The setup with a long-pass filter and then a coupling into the fiber bundle proved cumbersome, so in one exemplary implementation the long-pass filter was excluded and instead the silica Raman background noise generated in the fiber bundle by the excitation light was recorded. Because of the 785 nm laser side band and Raman spectra generated by the PCF cladding jacket and the fiber bundle, the acquired spectra were not completely clean. Therefore, the silica Raman spectra of the collecting fiber bundle was subtracted from the recorded Raman spectrum of the ethanol-filled fiber with collecting fiber bundle, to give the pure ethanol Raman spectrum as shown in FIG. 4. Note that in FIG. 4 the pure ethanol Raman spectrum does not have the same Raman signal count scale, but is expanded for clarity.

Figure 5:
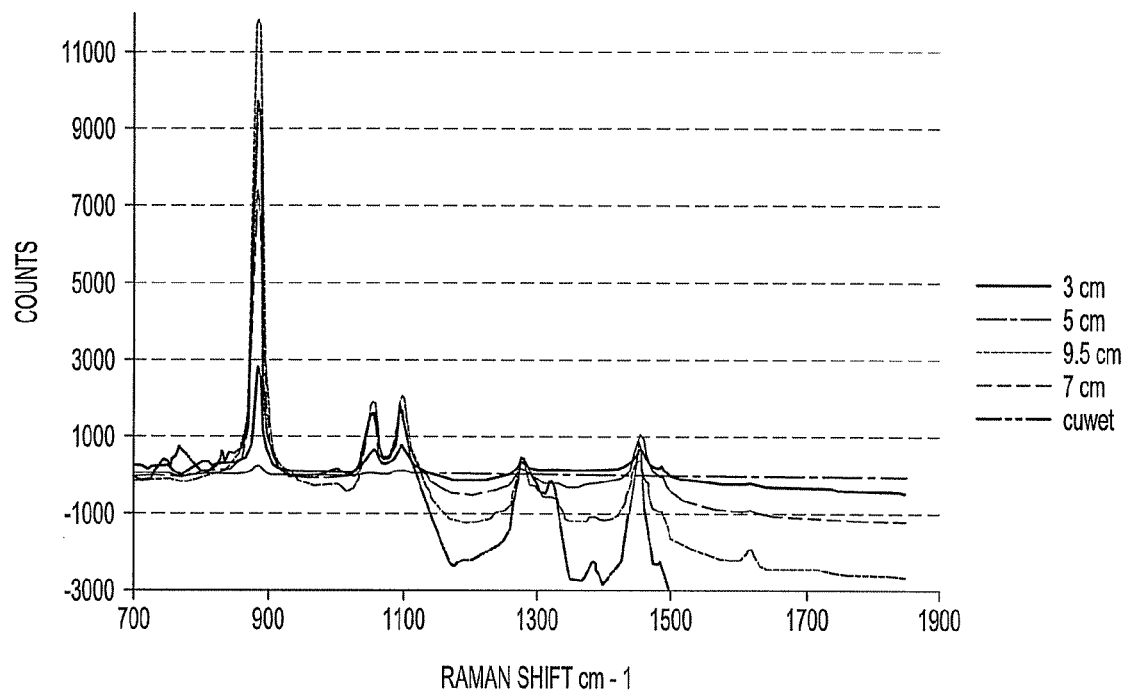
FIG. 5 illustrates the Raman spectra for pure ethanol determined with photonic crystal fiber having different lengths.

To derive a Raman signal enhancement factor from the non-selectively filled PCF, the ethanol spectra from 3, 5, 7, and 9.5 cm of filled PCF were acquired and compared with the Raman spectrum from a 1 cm path-length ethanol-filled quartz cuvette as shown in FIG. 5. Using the 885 cm$^{-1}$ ethanol peak from each spectrum, ratios of peak heights were used to determine the enhancement at each PCF length. Because the PCF guiding loss increases by increasing Raman shift of spectrum, the spectrum lines with higher Raman shift attenuated more, this attenuation is proportion to the fiber length. Therefore, this non-uniformity of PCF attenuation as a function of Raman shift and PCF length can be easily seen.

Figure 6:
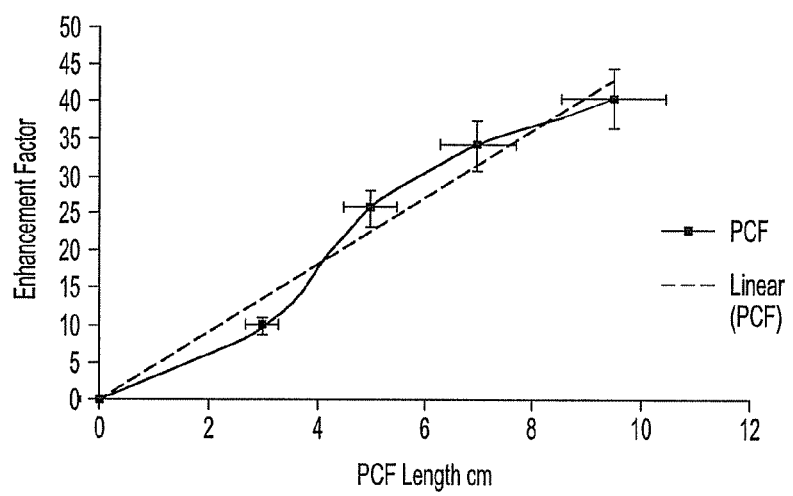
FIG. 6 illustrates a relative enhancement factor for different length fibers as compared to a 1 cm length quartz cuvette.

FIG. 6 shows the enhancement factor measurements in non-selective ethanol filled PCF as a function of PCF length. In theory, for spontaneous Raman spectrum we expect a linear relation, by ignoring fiber loss for short fiber lengths between the interaction length and Raman enhancement factor (dashed line in FIG. 6). Therefore, a good correlation between the theory and our measurements was observed. Thus, a novel Raman spectroscopy platform is provided by filling HC-PCF non-selectively. The simplicity of this method, having reasonable Raman signal enhancement combined with the high degree of overlap of the propagating mode with the analyte and small sample volumes required, makes it a promising candidate for sensitive and low-power identification of biological specimens.

Furthermore, large enhancement can be obtained through surface enhanced Raman spectroscopy. In surface enhanced Raman spectroscopy, an analyte is chosen that will adsorb (attract) to surface of metal nanoparticle (e.g., having a size of 20-100 nm) and will result in electromagnetic and chemical enhancement. The metal nanoparticles can be deposited on the inner walls of the cladding channels or merely contained in the solvent with the analyte of interest; otherwise, the method for using a photonic crystal fiber for biosensing is as described above.

An exemplary application for the Raman spectroscopy platform described above is the measurement of heparin or other blood parameters. As optical methods are well-suited for measurement of relative changes in blood parameters, they are ideal for monitoring changes in blood resulting from large administered doses of heparin during heart surgery. If heparin can be accurately monitored optically, continuous readout could be made available during surgery, resulting in improved and early detection of potentially life-threatening blood clotting events. By filling a photonic crystal fiber with blood, it can serve a dual purpose. The first is as a Raman enhancer as light interacts with matter for longer interaction length as well as a nano container.

In an exemplary arrangement, the fiber is configured as an interchangeable sample container (e.g., a test tube). For example, the fiber may be contained in a small needle like container with a small opening lid on the top to insert blood samples for testing. In order to measure heparin content the only thing to be done is to fill the fiber with blood and place it in a space provided in the apparatus for heparin measurement. The light is coupled into the filled fiber, after passing long pass filter the output light is collected by a detector and processed through a processor for determining the concentration of heparin in blood. Other applications for the Raman spectroscopy platform described herein are also contemplated by this disclosure.

The above description is merely exemplary in nature and is not intended to limit the present disclosure, application, or uses.

What is claimed is:

1. A method of biosensing using a photonic crystal fiber having a hollow core surrounded by a cladding with a plurality of channels, comprising:
   designating an analyte of interest;
   determining a wavelength for an excitation light source which generates a Raman spectrum when incident upon the analyte of interest;
   selecting a photonic crystal fiber which accounts for a bandgap shift when the photonic crystal fiber is filled with a solvent hosting the analyte of interest;
   filling the hollow core and the entirety of the cladding channels of the photonic crystal fiber with the solvent; and
   interrogating the analyte of interest by coupling light from the light source to the photonic crystal fiber.

2. The method of claim 1 further comprises analyzing the light output from the photonic crystal fiber for a spectrum of spontaneously scattered Raman-shift light.

3. The method of claim 1 further comprises evaluating the analyte of interest based upon Raman spectrum experienced by the light output from the photonic crystal fiber.

4. The method of claim 1 wherein selecting a photonic crystal fiber further comprises:
   determining a refractive index for the solvent used to fill the photonic crystal fiber; and
   computing a bandgap shift caused by non-selectively filling of the photonic crystal fiber using refractive index scaling laws.

5. The method of claim 4 wherein computing a bandgap shift is determined in accordance with $$\lambda' = \lambda_0 \left[ \frac{1 - \left(\frac{\eta_{liq}}{\eta_{sil}}\right)^2}{1 - \left(\frac{\eta_{air}}{\eta_{sil}}\right)^2} \right]^{1/2}$$

where $\lambda_o$ is a central wavelength of the bandgap of the photonic crystal fiber with an empty core; $\lambda'$ is a central wavelength of a shifted bandgap of the filled photonic crystal fiber;

$\eta_{liq}$ is a refractive index of the liquid sample, $\eta_{air}$ is a refractive index of air and $\eta_{sil}$ is a refractive index of silica.

6. The method of claim 1 further comprises enhancing the Raman signal experienced by the light output from the photonic crystal fiber by increasing length of the photonic crystal fiber.

7. A method of biosensing using a photonic crystal fiber having a hollow core, comprising:
designating an analyte of interest;
determining a wavelength of light that generates a Raman spectrum when incident upon the analyte of interest;
determining a refractive index of a solvent used to host the analyte of interest;
selecting a photonic crystal fiber that would guide the light when the fiber is non-selectively filled with the solvent using refractive index scaling laws;
filling the selected photonic crystal fiber non-selectively with the solvent having the analyte of interest;
coupling light from a light source to the photonic crystal fiber; and
evaluating the analyte of interest by analyzing the light output from the photonic crystal fiber.

8. The method of claim 7 further comprises analyzing the light output from the photonic crystal fiber for a spectrum of spontaneously scattered Raman-shift light.

9. The method of claim 7 further comprises analyzing the light output from the photonic crystal fiber for a Raman spectrum and evaluating the analyte of interest based upon the Raman spectrum experienced by the light output from the photonic crystal fiber.

10. A biosensor comprising:
a photonic crystal fiber having a hollow core surrounded by a porous cladding, where core and cladding of the photonic crystal fiber is filled with a sample having an analyte of interest;
an excitation light source optically coupled to an input of the photonic crystal fiber; and
a light detector optically coupled to an output of the photonic crystal fiber and configured to detect a spectrum of spontaneously scattered Raman-shift light received from the photonic crystal fiber.

11. The biosensor of claim 10 further comprises an objective lens that optically couples the light source to the photonic crystal fiber.

12. The biosensor of claim 11 further comprises a band pass filter arranged to pass light from the light source to the objective lens.

13. The biosensor of claim 10 further comprises a multimode fiber bundle arranged to collect light output from the photonic crystal fiber.

14. The biosensor of claim 10 further comprises a long pass filter arranged to pass light output from the photonic crystal fiber to the light detector.

15. The biosensor of claim 10 wherein the light detector is further defined as a spectrograph.

16. A method of biosensing using a photonic crystal fiber having a hollow core surrounded by a cladding with a plurality of channels, comprising:
designating a metal nanoparticle that will be deposited on inner walls of the cladding channels;
designating an analyte of interest that will be adsorbed to the metal nanoparticles;
determining a wavelength of light that generates a Raman spectrum when incident upon the analyte of interest;
selecting a photonic crystal fiber that would guide the light when the fiber is non-selectively filled with a solvent using refractive index scaling laws;
filling the selected photonic crystal fiber non-selectively with the solvent having the analyte of interest and the designated metal nanoparticles;
coupling light from a light source to the photonic crystal fiber; and
evaluating the analyte of interest by analyzing the light output from the photonic crystal fiber.

* * * * *